United States Patent
Peltier

(10) Patent No.: US 6,346,087 B1
(45) Date of Patent: Feb. 12, 2002

(54) FLASK FOR PREPARING A CYTOLOGICAL SUSPENSION

(75) Inventor: Eric Peltier, 16 rue des Morteaux 92160, Antony (FR)

(73) Assignees: Labonord, Templemars (FR); Eric Peltier, Antony (FR)

(*) Notice: Subject to any disclaimer, the term of this patent is extended or adjusted under 35 U.S.C. 154(b) by 0 days.

(21) Appl. No.: 09/550,098

(22) Filed: Apr. 14, 2000

(30) Foreign Application Priority Data

Apr. 14, 1999 (FR) .............................. 99 04664

(51) Int. Cl.⁷ .............................................. A61B 10/01
(52) U.S. Cl. ...................................................... 600/569
(58) Field of Search ............................. 600/572, 567, 600/570, 571

(56) References Cited

U.S. PATENT DOCUMENTS

| | | |
|---|---|---|
| 3,815,580 A | 6/1974 | Oster |
| 3,828,765 A | 8/1974 | McDonald |
| 3,954,563 A * | 5/1976 | Mennen ...................... 600/572 |
| 4,439,319 A | 3/1984 | Rock |
| 4,633,886 A | 1/1987 | Bucaro, Jr. |
| 5,102,250 A * | 4/1992 | Gueret ........................ 401/126 |
| 5,422,273 A | 6/1995 | Garrison et al. |
| 5,833,928 A | 11/1998 | Ratajczak et al. |
| 5,947,622 A * | 9/1999 | Akyildiz et al. ............ 401/129 |
| 5,991,617 A * | 11/1999 | Couch et al. ............... 206/15.3 |
| 6,063,038 A * | 5/2000 | Diamond et al. ........... 600/569 |
| 6,207,113 B1 * | 3/2001 | Kagaya ...................... 422/102 |

FOREIGN PATENT DOCUMENTS

EP 0 175 326 3/1986

* cited by examiner

Primary Examiner—Robert L. Nasser
Assistant Examiner—Pamela Wingood
(74) Attorney, Agent, or Firm—Young & Thompson

(57) ABSTRACT

This flask for preparing a fixative-based cytological suspension, which flask is provided with an opening (5) which is intended for receiving a brush (3) for cytological sampling, which brush is detachably fastened to a manipulation handle (4), is such that the opening (5) of the flask comprises abutment means (6) for the brush, which means enable the brush to be locked in the flask and to be detached from the handle (4), and at least one portion of perforated screen (6) for filtering the suspension during pouring.

7 Claims, 1 Drawing Sheet

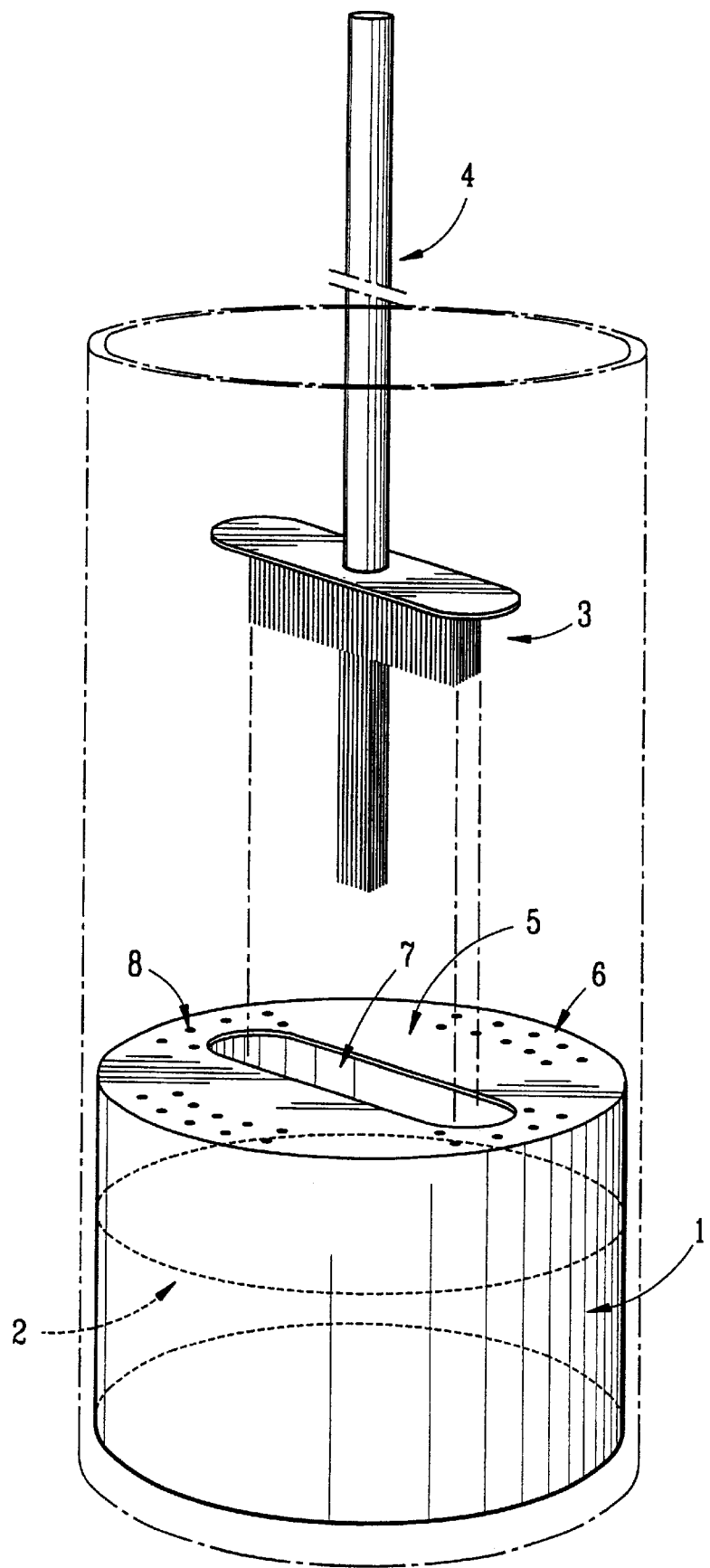

FLASK FOR PREPARING A CYTOLOGICAL SUSPENSION

FIELD OF THE INVENTION

The present invention relates to a flask for preparing a fixative-based cytological suspension.

BACKGROUND OF THE INVENTION

Such flasks are used in the state of the art for preparing cervical or vaginal cytological suspensions which are to be analyzed.

The cervical or vaginal samplings are performed by medical practitioners using special brushes which are detachably fastened to manipulation handles.

Once the sampling has been performed, the practitioner plunges the brush into the flask and detaches it from the handle, so as to enable the sampled cells to become deposited in the fixative.

However, undesirable constituents can also become deposited in the fixative, such as debris recovered by the brush during the sampling (mucous, aggregations, etc.), squamae which derive from the practitioner and which become deposited in the flask, in particular when the brush is being manipulated in order to detach it from the handle, etc.

These constituents can be very troublesome when the suspension is subsequently being analyzed.

SUMMARY OF THE INVENTION

The aim of the invention is therefore to solve these problems.

To this end, the invention relates to a flask for preparing a fixative-based cytological suspension, with this flask being provided with an opening which is intended for receiving a brush for cytological sampling, which brush is detachably fastened to a manipulation handle, wherein the opening of the flask comprises abutment means for the brush, which means enable the brush to be locked in the flask and to be detached from the handle, and at least one portion of perforated screen for filtering the suspension during pouring.

BRIEF DESCRIPTION OF THE DRAWING

The invention will be more thoroughly understood from reading the description which follows, which is given solely by way of example and which is presented while referring to the attached drawing, which depicts a perspective view of an example of an embodiment of a flask according to the invention.

DETAILED DESCRIPTION OF THE INVENTION

Thus, this FIGURE depicts an example of an embodiment of a flask 1 for preparing a cytological suspension, for example a cervical or vaginal cytological suspension.

This flask is intended for receiving a cell fixative, which is designated by the general reference number 2, and a sampling brush, which is designated by the general reference number 3 and which is detachably fastened, in the usual manner, to a manipulation handle 4.

After sampling, this brush is introduced into the flask through an open end 5 of this flask.

According to the invention, this open end 5 of the flask comprises abutment means for the brush, which means enable the brush to be locked in the flask once the practitioner has introduced it into the flask and therefore to be detached from the handle by simply drawing on the latter, for example, so that the brush falls into the fixative.

This then avoids any manipulation of the brush by the practitioner as he is depositing it in the flask and thus reduces the risk of contaminating the suspension with squamae, etc.

Furthermore, this end of the flask also comprises at least one portion of perforated screen which enables the suspension to be filtered during pouring while at the same time retaining the largest debris.

In the embodiment example depicted in this FIGURE, the open end 5 of the flask in fact comprises a transverse screen 6 which is provided with a hole 7 which is, for example, centered on the axis of the flask and which allows the sampling brush 3 to pass through with a view to its being introduced into the flask.

In fact, the brush 3 and the corresponding hole 7 of the screen 6 can exhibit complementary oblong shapes, thereby allowing the brush to be introduced into the flask in accordance with a specific angular orientation.

If the practitioner turns the brush slightly in the flask, the brush can then come to abut against the lips of the screen 6 which delimit this hole 7 for the purpose of locking the brush 3 in the flask and detaching it from the handle 4 by pulling on the latter.

The practitioner is not therefore induced to touch the brush or the handle in the vicinity of the brush when he wishes to detach the latter from this handle.

Furthermore, such a structure is designed for single use by rendering it more difficult to recover the brush with a view to reusing the latter, as it was possible to do, with the risks which this entailed.

In the example described in this FIGURE, perforations are also envisaged in the screen 6 around the hole 7 in this screen.

These perforations are, for example, distributed regularly around this hole.

As has previously been pointed out, this makes it possible to filter the suspension during pouring.

This flask can, for example, be made of a plastic material or some other material.

It goes without saying, of course, that other embodiments of this flask can also be envisaged.

What is claimed is:

1. A flask for preparing a fixative-based cytological suspension, with this flask (1) being provided with an opening (5) which is intended for receiving a brush (3) for cytological sampling, which brush is detachably fastened to a manipulation handle (4), wherein the opening (5) of the flask comprises abutment means (6) for the brush and at least one portion of perforated screen (6) for filtering the suspension during pouring, said abutment means enabling the brush to be locked in the flask and to be detached from the handle (4).

2. The flask as claimed in claim 1, wherein the opening of the flask is sealed off by a screen (6) which is provided with a hole (7) for the passage of the sampling brush (3) and whose lips delimiting this hole form abutment means for this brush and at least one portion of which is perforated (8) for filtering the suspension during pouring.

3. The flask as claimed in claim 2, wherein the hole (7) of the screen is centered on the axis of the flask (1).

4. The flask as claimed in claim 1 wherein filtration perforations (8) are regularly distributed in the screen (6) of the opening of the flask around the hole (7) of this screen.

5. The flask as claimed in claim 1 wherein the sampling brush (3) and the hole (7) of the screen exhibit complementary oblong shapes.

6. The flask as claimed in claim 1 wherein the suspension is a cervical cytological suspension.

7. The flask as claimed in claim 1 wherein the suspension is a vaginal cytological suspension.

* * * * *